US00RE35941E

United States Patent [19]

Stansbury, Jr.

[11] E Patent Number: Re. 35,941

[45] Reissued Date of Patent: Nov. 3, 1998

[54] MECHANICAL TOOTHBRUSH

[75] Inventor: Benjamin H. Stansbury, Jr., Alexandria, Va.

[73] Assignee: Pulse Innovations, Inc., Ontario, Canada

[21] Appl. No.: 552,113

[22] Filed: Nov. 2, 1995

Related U.S. Patent Documents

Reissue of:

[64] Patent No.: 5,259,083
Issued: Nov. 9, 1993
Appl. No.: 950,174
Filed: Sep. 24, 1992

[51] Int. Cl.[6] ..... A61C 17/32; A61C 17/34

[52] U.S. Cl. ..... 15/22.2; 15/22.1; 433/122

[58] Field of Search ..... 15/22.1, 22.2, 15/201, 97.1, 184, 22.4, 28, 29; 601/139, 141, 142; 433/216, 122

[56] References Cited

U.S. PATENT DOCUMENTS

| | | | |
|---|---|---|---|
| 1,255,028 | 1/1918 | Leonard et al. | 15/22.1 |
| 1,517,320 | 12/1924 | Stoddart | 15/22.1 |
| 2,267,916 | 12/1941 | Hersey | 15/22.1 |
| 2,601,567 | 6/1952 | Steinberg | 15/167.1 |
| 2,935,755 | 5/1960 | Leira et al. | 15/167.1 |
| 3,110,918 | 11/1963 | Tate, Jr. | 15/167.1 |
| 3,160,902 | 12/1964 | Aymar | 15/22.1 |
| 3,683,442 | 8/1972 | Holly | 15/201 |
| 3,935,869 | 2/1976 | Reinsch | 15/22.1 |
| 4,156,620 | 5/1979 | Clemens | 15/22.1 |
| 4,223,417 | 9/1980 | Solow | 15/22.1 |
| 4,346,492 | 8/1982 | Solow | 15/22.1 |
| 4,735,200 | 4/1988 | Westerman | 15/22.2 |
| 4,995,131 | 2/1991 | Takeda | 15/22.1 |

FOREIGN PATENT DOCUMENTS

| | | |
|---|---|---|
| 0 135 946 | 4/1985 | European Pat. Off. . |
| 33 06 176 | 8/1984 | Germany . |
| 358 408 | 1/1962 | Switzerland . |
| 2247297 | 2/1992 | United Kingdom . |

*Primary Examiner*—Gary K. Graham
*Attorney, Agent, or Firm*—Finnegan, Henderson, Farabow, Garrett & Dunner, L.L.P.

[57] ABSTRACT

A power driven mechanical toothbrush is disclosed. A replaceable toothbrush head member has tuft blocks retained generally therewithin and extending laterally outwardly from the a cam shaft. Each tuft block has at least one tuft of bristles, usually four, secured within the tuft block and extending upwardly therefrom. Each of the bristles has a distal end at a distance from its tuft block, and the bristles in each tuft are generally parallel to each other. The toothbrush head member is adapted to receive and retain the tuft blocks in sliding relation therein, so that each tuft block slides linearly in a direction parallel to the longitudinal tuft axis as guided by guide rails within the head member, between a retracted position and an extended position. Each tuft block is driven from its retracted position to its extended position by the rotatable cam shaft. In use, the tuft bristles are brought into contact with the teeth by the user, before the respective tuft block reaches its extended position, so as to thereby flex the bristles and to cause a lateral motion of the distal of the bristles along the surface of the teeth. The reciprocating action of the tuft blocks causes a wiping action of the bristles and bristle ends against the teeth, and the teeth are thereby cleaned.

82 Claims, 5 Drawing Sheets

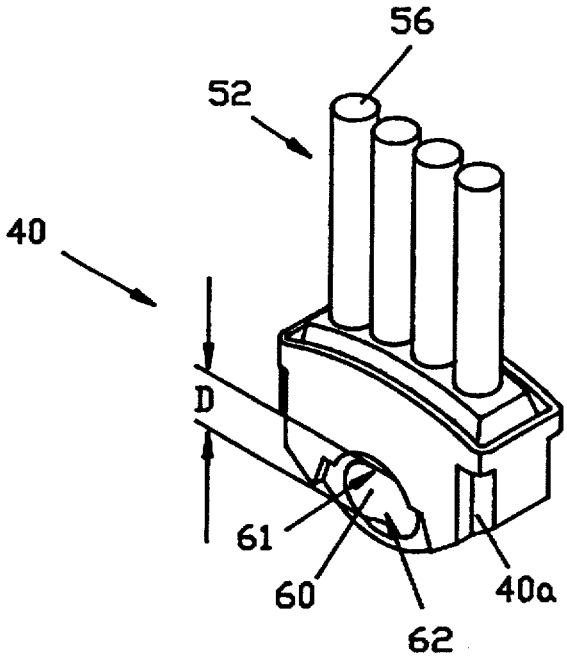
FIG. 9
FIG. 10
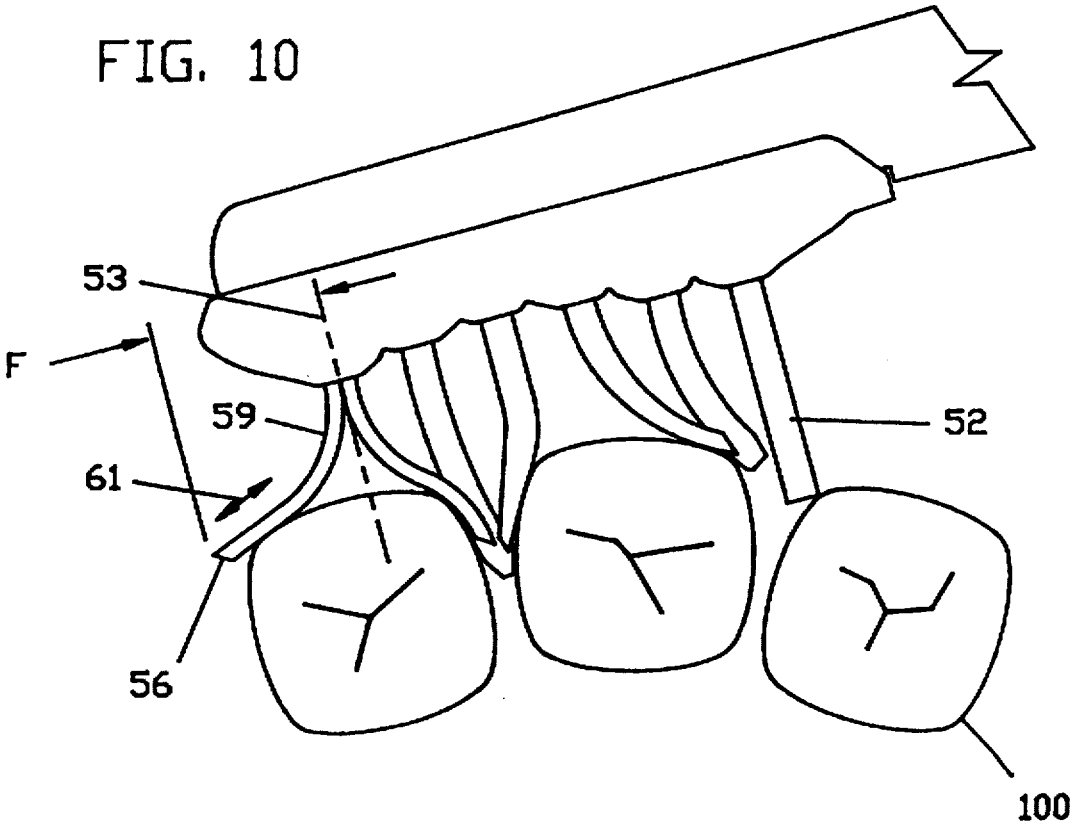

MECHANICAL TOOTHBRUSH

Matter enclosed in heavy brackets [ ] appears in the original patent but forms no part of this reissue specification; matter printed in italics indicates the additions made by reissue.

FIELD OF THE INVENTION

This invention relates to toothbrushes and more particularly to portable hand-held mechanical toothbrushes. Specifically, a novel toothbrush head is disclosed.

BACKGROUND OF THE INVENTION

Manual toothbrushes of one form or another have been used to clean teeth for many years. Depending on the exact technique used in conjunction with such manual toothbrushes, results obtained through their use are generally adequate.

Mechanical, and especially electromechanical toothbrushes that provide a means for an individual to brush his teeth more effectively, properly and thoroughly than by use of a simple manual toothbrush, have been available for several years. Most of these mechanical or electromechanical toothbrushes rotate or oscillate in some manner so as to vigorously clean the teeth. Typically, electromechanical toothbrushes are powered by rechargeable batteries that power an electric motor that in turn drives the toothbrush head or heads. It has been found that in general such electromechanical toothbrushes do indeed produce improved results compared to brushing with a manual toothbrush.

There is a technique, which is known among professionals as the "Bass Technique", that can be used to achieve superior results in terms of cleaning one's teeth through use of a manual toothbrush. In basic terms, the "Bass Technique" requires the user to position the brush over a zone of the teeth use very short strokes to vibrate the brush so as to "brush" that zone of the teeth as described above for a period of time sufficient to remove foreign material therefrom. These short strokes are made in a direction transverse to the orientation of the bristles. Towards the end of a given stroke, the bristles flex so as to become oriented such that the ends thereof point generally away from the direction of travel of the bristles across the teeth. At this point, the bristles have started to sweep across the teeth, which is not very effective for removing foreign material from the teeth, and therefore the direction of the stroke is changed, and a new stroke begun in the opposite direction. At the beginning of this new stroke, the still flexed bristles are pointed in the direction of the stroke which causes the bristle to chisel the foreign material from the teeth for a moment before the bristles again flex so as to again sweep across the teeth. Generally, this type of brushing takes more than 20 strokes at each separate location and there are typically about 40 different brush locations that are required to brush all of a person's teeth. At a vigorous pace of three strokes per second, this procedure would take over four minutes using a manual toothbrush, which is unacceptably lengthy. It has been found that for virtually any procedure for cleaning the teeth, most people are apt to quit brushing after about one minute. This means that in the case of the "Bass Technique", the cleaning procedure would normally not be done properly using a manual toothbrush.

The advantage of using the "Bass Technique" is that the bristles are emulating a chiseling action, instead of a sweeping action, and this is the most effective way of removing foreign material from the teeth.

It is believed that superior results would also be possible through use of a mechanical or electromechanical toothbrush that takes advantage of the chisel type cleaning demonstrated by the "Bass Technique". Indeed, it is possible that the chiseling action demonstrated by the "Bass Technique" could be improved on by providing a more direct chiseling and flexing action of the bristles. In order to do this, such a toothbrush would need to have bristles that approach the teeth substantially directly along the longitudinal axis of each bristle and then bends slightly, so that each bristle chisels and generally undercuts any foreign material from the teeth so as to lift the foreign material away.

As will be discussed in greater detail hereafter, the present invention provides a mechanical or electromechanical toothbrush that will effectively emulate the "Bass Technique". The toothbrush that is provided by the present invention may be used, in the sense of the manner that it is held in the hand and somewhat in the manner that it is moved around the mouth, in much the same manner as a conventional toothbrush. Thus, the mechanical action of the present invention will provide for the bristles to thrust forwardly in a direction that is generally perpendicular to the teeth, along the longitudinal axes of the bristles, and the bristles will flex or bend slightly when they contact the teeth due to the pressure being applied against them by the user as he holds the toothbrush. However, the bristles of the toothbrush then exhibit a mechanical oscillating action in short strokes along their longitudinal axes, which occurs as a consequence of the bristles being mechanically driven. As the user manipulates the toothbrush of the present invention in much the same manner as an ordinary toothbrush would be manipulated, the pressure of the brush against the teeth deflects the bristles of the toothbrush around the complex topography of the teeth. Thus, the cleansing action which is somewhat as a chisel or scraper would act against a surface will generally undercut any foreign material, which is then lifted or washed away. That cleansing or cleaning action occurs as the distal end of the bristles which are more or less tangential, or at least at an acute angle, to the tooth surfaces.

In action, therefore, the mechanical bristle action occurs such that the original stroke which is imparted to the bristle is transmitted to where the bristle end is flexed, so that the tip of each bristle moves in the same direction as the bristle axis, with a positive or negative motion of the bristle end in that direction as a consequence of the reciprocating motion imparted to the bristles.

Other known techniques, especially of prior mechanically driven toothbrushes, merely sweep the high spots, never entering the area between the teeth or the small irregularities in the teeth. Various types of toothbrushes that use these other known techniques are discussed hereafter, with respect to the Prior Art.

PRIOR ART

One type of prior art falls under the category of rotating brush heads. Electric toothbrushes that have rotating brush heads or tufts merely "sweep" the ends of the bristles of the brush heads across the teeth and cannot effectively clean between the teeth or clean in the irregular surfaces of the teeth.

A second type of prior art is an electric toothbrush having reversing rotating brush heads. Such a toothbrush is exemplified in U.S. Pat. No. 4,156,620 issued May 29, 1979 to CLEMENS, which discloses an Apparatus and Method for Cleaning Teeth. The apparatus has a plurality of short and long tufts that are driven in a reversing rotating manner by a reciprocating gear rack that is in turn driven by crank arm. The crank arm is driven by a crown gear that is in turn driven by a smaller crown gear that is driven by an electric motor. Again, the brush heads or tufts merely "sweep" the ends of the bristles of the brush heads across the teeth for most of the rotating action. As the rotating heads change direction, the bristles can momentarily push directly onto the teeth and to some degree chisel the foreign material on the teeth.

The third type of prior art mechanized toothbrush is one that performs a scrubbing action, which is basically analogous to a scrub brush cleaning a floor, especially a textured contoured floor. The brush is moved back and forth over the teeth, preferably with vigorous short back and forth strokes. Each bristle basically sweeps over the tooth over most of its stroke. At the end of each stroke, where the direction of the brush is changed, the ends of the bristles can momentarily push directly onto the teeth and to some degree chisel the foreign material on the teeth. Initially, when the change in direction occurs, the bristle is pointing in the new direction of the upcoming stroke until pushed back by friction, wherein it resumes its passive sweeping motion. Mechanized toothbrushes having scrubbing actions are exemplified by the following three patents.

U.S. Pat. No. 1,517,320 issued Dec. 2, 1924 to STODDART discloses an electromechanical toothbrush having a plurality of sections, each section mounted on a central shaft, with the sections juxtaposed to one another. Each section is driven by a separate eccentric that is in turn rotated by a central shaft. The sections are precluded from rotating 360° by two opposed fulcrum points, one on each side of the sections. Each section is rotated somewhat eccentrically until the side of the section contacts the appropriate fulcrum point, which contact stops the rotating. The bristle portions of each section basically move across the teeth, thus giving a scrubbing action. Alternating sections move in opposed directions.

U.S. Pat. No. 3,160,902 issued Dec. 15, 1964 to AYMAR discloses an electromechanical toothbrush wherein the brush portion oscillates along its longitudinal axis and also oscillates back and forth around its longitudinal axis. An electric motor turns a small beveled gear which in turn rotates a larger beveled gear. The large beveled gear drives a crank pin that is connected to the brush rod, onto which the brush is securely attached.

Swiss Patent 358,408 to WYDLER discloses an electromechanical toothbrush having a toothbrush head that oscillates about a central area defined by a central axis. The toothbrush head is driven by a pair of parallel rotating drive shafts with eccentric ends that alternatingly push opposite sides of the toothbrush forward towards a person's teeth. The drive shafts are rotated by a single gear attached to a motor drive shaft. It would appear that such a unit would cause excessive vibration in a person's mouth when used.

A fourth type of mechanical toothbrush is a reciprocating mechanical toothbrush where the reciprocation is generally in a direction parallel to the axis of the bristles; which is basically the same classification as the present invention. There are three such prior art devices known, and in these prior art devices, as well as in the present invention, the bristles of the toothbrush reciprocate back and forth along their longitudinal axis so as to basically impact against the teeth. These three prior art patents will now be described.

U.S. Pat. No. 2,935,755 issued May 10, 1960 to LEIRA et al, discloses a toothbrush having a plurality of bristles that move in and out of a toothbrush head along their longitudinal axis. These bristles are passively operated by the action of the toothbrush head over a person's teeth. The bristles are pushed into the toothbrush head by way of contact with a person's teeth, and pushed outwardly against the person's teeth by means of a flexible band spring member. No chiseling action takes place, whatsoever.

U.S. Pat No. 4,346,492 issued Aug. 31, 1982 to SOLOW, discloses a mechanical toothbrush with individual tuft drives wherein individual tufts of bristles are pneumatically driven along their respective longitudinal axes to impact generally perpendicularly on a person's teeth. One important aspect of the SOLOW invention, as emphasized in that patent, is that due to the pneumatic powering of the tufts of bristles, each tuft stops when it impacts the teeth, and therefore there is no true chiseling effect. Indeed, the bristles in the SOLOW toothbrush are generally short and stiff so that they do not flex. Further, the bristles are directed towards the teeth all at the same time, and therefore, according to Newton's third law of motion, cause the head of the toothbrush to essentially vibrate oppositely to the tufts, which causes excessive and undesirable vibration against a person's mouth.

A further U.S. Pat. No. 4,223,417 issued Sep. 23, 1980 to SOLOW, discloses a gliding, mechanized toothbrush having a pair of opposed toothbrush pistons that are positioned to each contact one side of a tooth at the same time. These pistons oscillate up and down both within a common head such that the bristles of each piston are moved in a direction along the longitudinal axes of the bristles. The pistons are pneumatically powered which causes the same problem of stopping at impact, as discussed with respect to SOLOW U.S. Pat. No. 4,346,492. Further, the bristles on each piston are not separated into sections, and it is therefore easy for a few bristles to contact the teeth and slow down or even stop the action of the piston.

SUMMARY OF THE INVENTION

A power driven mechanical toothbrush is disclosed. The power driven mechanical toothbrush comprises a cam shaft adapted to be rotatably driven, and having a central longitudinal axis, and a driving means adapted to rotatably drive said cam shaft. There is a toothbrush head member having a centrally disposed longitudinal head axis, a bottom wall, an end wall, and a pair of opposed side walls. At least one tuft block—usually four to seven blocks are used—is retained generally within the toothbrush head member extending laterally outwardly from the central longitudinal axis. One tuft block is used for a proximal toothbrush whose purpose is specifically to clean and massage the gingival margins and interproximal areas of the teeth.

The at least one tuft block has at least one tuft of bristles—usually four tufts are used—secured within the tuft block and extending upwardly therefrom. The bristles have a distal end at a distance from the tuft block, and the bristles and tufts of bristles are all generally parallel to each other. Each bristle tuft has a longitudinal tuft axis located generally along the centre thereof. The toothbrush head member is adapted to receive and retain the tuft block or tuft blocks in sliding relation therein, such that the tuft block or tuft blocks slide linearly in a direction parallel to the longitudinal tuft axes, as guided by guide means within the head member. Each tuft block slides between a tuft block retracted position and a tuft block extended position. Each tuft block is driven from its tuft block retracted position to its tuft block extended position by the rotation of the cam shaft and the resulting interaction between the cam shaft and the tuft block.

In use, the bristles impact the teeth of a user before the respective tuft block reaches its extended position, so as to flex the bristles and cause a lateral motion of the distal end thereof along the tooth surface, thereby to remove unwanted substances from the teeth.

BRIEF DESCRIPTION OF THE DRAWINGS

Embodiments of the present invention will now be described by way of the accompanying drawings, in which:

FIG. 9 is an isometric view of a tuft block having tufts inserted therein;

FIG. 10 is a view similar to FIG. 3, showing a toothbrush in use against the teeth of a user;

DETAILED DESCRIPTION OF THE PREFERRED EMBODIMENTS

Figure 1:
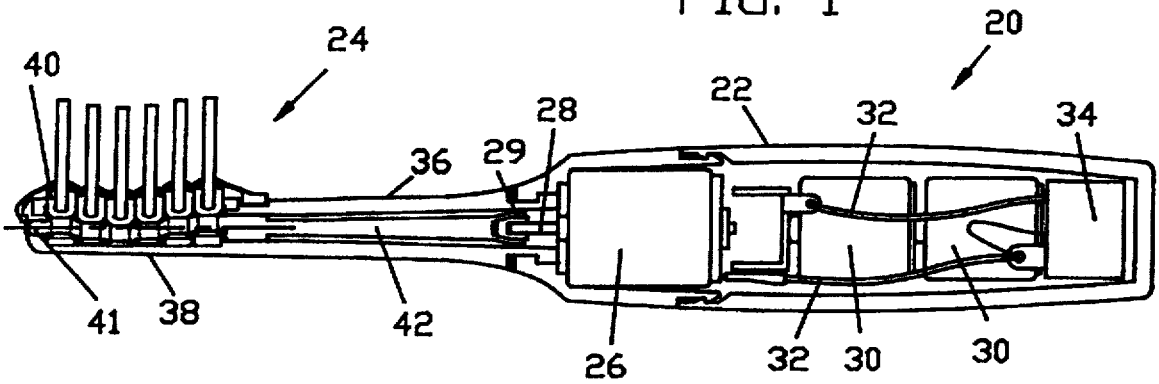
FIG. 1 is a cut-away side view of a preferred embodiment of the toothbrush of the present invention.

Reference will now be made to FIG. 1 which shows the toothbrush 20 of the present invention having a two-part main housing 22 and a toothbrush head member 24 removably attached thereto. Within the main housing 22 is a high speed electrical motor 26 that acts as a driving means and has a drive shaft 28 extending therefrom into the toothbrush head member 24. The interfacing of the drive shaft 28 with the toothbrush head member 24 will be discussed in greater detail subsequently. Powering the high speed electrical motor 26 are batteries 30, which are connected to the electrical motor 26 by wires 32. Preferably, the batteries 30 are rechargeable and an induction coil or other charger circuit 34 exists within the main housing 22 so as to allow for charging of the batteries 30.

The toothbrush head member 24 mounts on the main housing 22 by way of an elongated shaft 36. Mounted within the head portion 38 of the toothbrush head member 24 is a plurality of tuft blocks 40 that fit through an opening 35 therein. In a preferred embodiment as illustrated, there are six tuft blocks 40. It is indeed possible to have any number of tuft blocks 40, with quantities of one through eight tuft blocks being contemplated as usable. The tuft blocks 40 slide up and down within the head portion 38 of the toothbrush head member 24 between an extended position and a retracted position, as will be described in more detail subsequently. The tuft blocks 40 are driven by way of a cam shaft 42 that fits through an aperture 60 in each of the tuft blocks 40. The cam shaft 42 is attached to the drive shaft 28 by way of attachment portion 29. The cam shaft 42 is thereby adapted to be rotatably driven by the driving means—the electrical motor 26.

Reference will now be made to FIGS. 2 through 10 in order to describe the workings of the toothbrush 20 of the present invention in detail. The head portion 38 of the toothbrush head member 24 includes a pair of opposed side walls 44, an end wall 46, and a bottom wall 48. There is a centrally disposed longitudinal head axis 50 along the head portion 38 of the toothbrush head member 24.

The tuft blocks 40 extend laterally outwardly from the central longitudinal axis 50 of the cam shaft 42. Each tuft block 40 has at least one tuft 52 of bristles 54 secured within the tuft block 40, and extending upwardly therefrom. Each tuft has a longitudinal tuft axis 53 located generally along the center thereof. The bristles 54 have a distal end 56 at a distance from the tuft blocks 40. Preferably, the bristles 54 extend outwardly from the tuft blocks 40 a distance of about ⅜ inches, and are of a diameter of about 0.005 to about 0.008 inches. The bristles 54 in the tuft blocks 40 are generally parallel to each other, and the tufts 52 are also generally parallel to each other within the same tuft block and also with respect to the tufts 52 in other tuft blocks 40. The preferred number of tufts 52 within a tuft block 40 is four; however, any number is acceptable with one tuft 52 per tuft block 40 to about six tufts 52 per tuft block 40 being contemplated as generally useful. The four tufts of bristles include two inner tufts and two outer tufts, with one inner and one outer tuft being disposed at each side of the longitudinal head axis 50. Generally, the outer or distal ends of the bristles and the tufts are even, but they may be contoured as to the ends of the individual bristles in a tuft or as to the ends of adjacent tufts.

Figure 8:
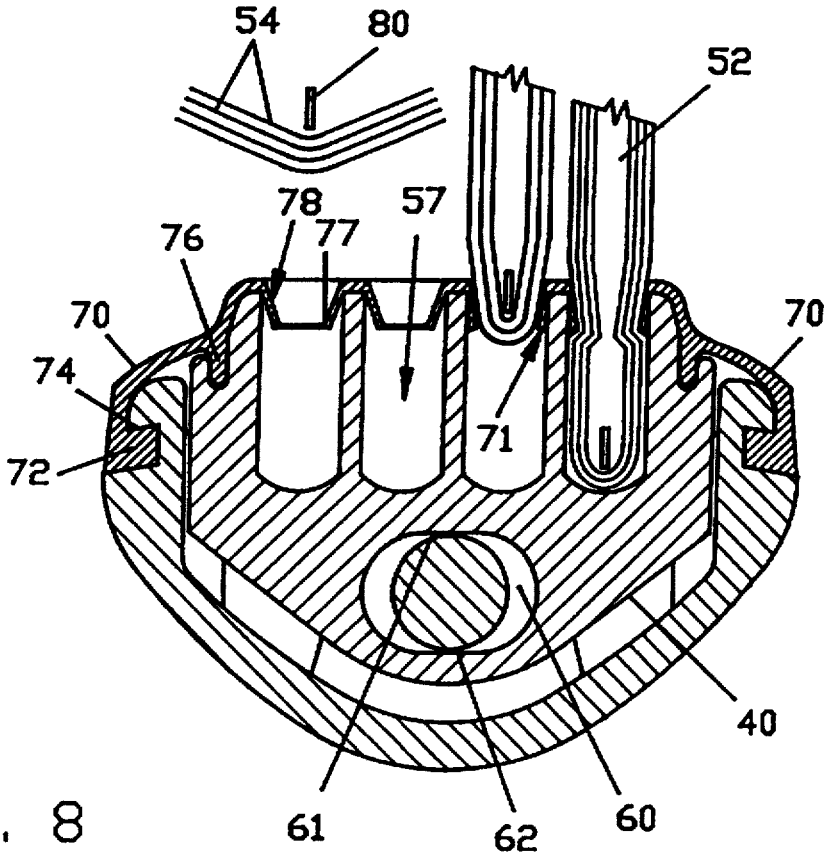
FIG. 8 is a partial enlarged cross-section view of a tuft block showing bristle tufts being inserted therein.

As shown in FIG. 8, the tufts 52 are inserted into the tuft blocks 40 in the following manner. The bristles 54 are bent around a wire pin or blade 80, which is preferably made of stainless steel, to form tufts. The tufts 52 are then forced into orifices 57 in the tuft blocks 40, in the manner of usual toothbrush manufacture. The ends of the pin or blade 80 are retained by interference of the pin or blade with the material of the tuft block into which it has been forced.

Figure 2:
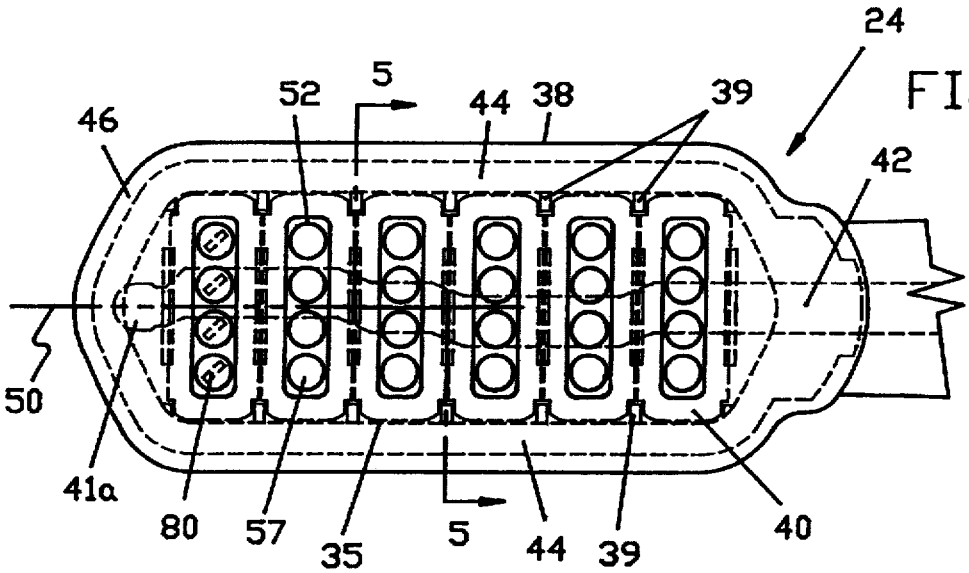
FIG. 2 is an enlarged top view of the toothbrush head member of the toothbrush of FIG. 1.

As can be best seen in FIG. 2, the tuft blocks 40 are substantially juxtaposed one to another and are disposed along the longitudinal head axis 50 of the toothbrush head member 24. The longitudinal tuft axes 53 are substantially perpendicular to the longitudinal head axis 50 of the elongated toothbrush head member 24.

The head portion 38 of the toothbrush head member 24 is adapted to receive and retain the tuft blocks 40 in sliding relation therein such that the tuft blocks 40 slide linearly in a direction parallel to the longitudinal tuft axes 53. The tuft blocks 40 are guided by guide means within the head portion 38 of the toothbrush head member, with these guide means comprising pairs of opposed guide rails 39. The opposed guide rails 39 extend inwardly from the opposed side walls 44. The tuft blocks 40 have indentations 40a (shown, for example, in FIG. 9) at the four corners thereof so as to accommodate the opposed guide rails 39.

The cam shaft 42 has a cam portion 43 at the one end thereof, at the opposite end to the attachment portion 29. The cam portion 43 of the cam shaft 42 has a plurality of lobes 45 thereon, each lobe 45 having a cam surface defining the perimeter thereof. Each lobe 45 is preferably substantially circular in cross-section, having a diameter "D", and is used to drive one tuft block 40 from its retracted position to its extended position. If there are six tuft blocks 40 in the toothbrush head member 24, there would correspondingly be six lobes 45 on the cam portion 43 of the cam shaft 42. The lobes 45 are connected by connecting portions 47, with the connecting portions 47 having a maximum thickness "D". The connecting portions 47 are ramped so as to facilitate positioning of the cam shaft 42 into the respective apertures 60 in each of the tuft blocks 40.

Figure 3:
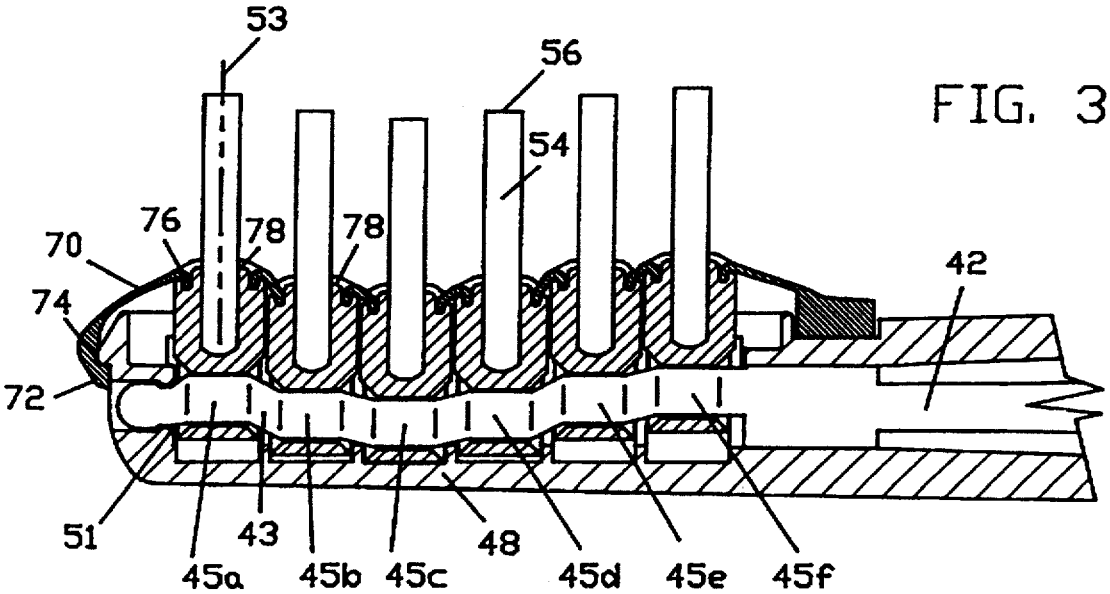
FIG. 3 is a side view of the toothbrush head member of FIG. 2.
Figure 4:
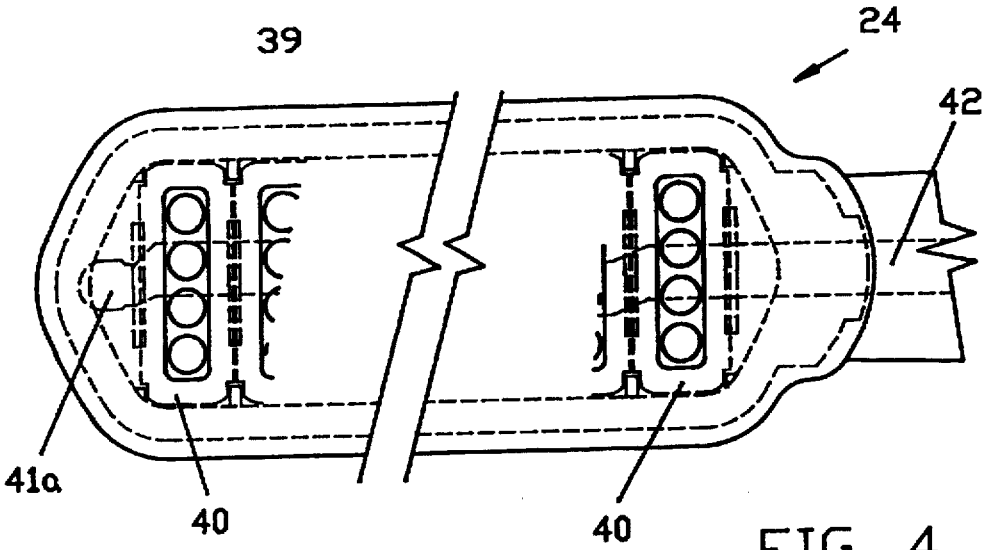
FIG. 4 is a top view similar to FIG. 2 except showing an undetermined number of tuft blocks.
Figure 5:
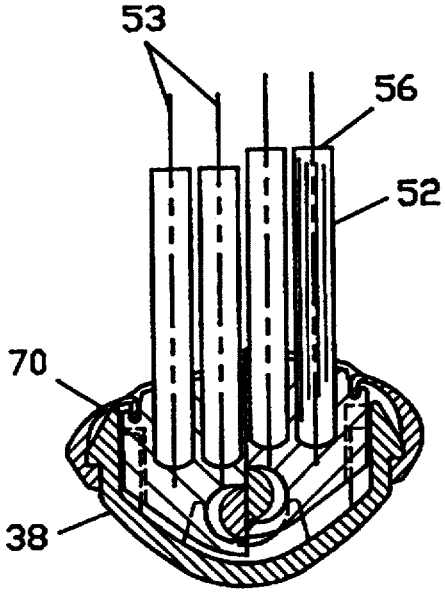
FIG. 5 is a cross-section of the toothbrush head along lines 5—5 of FIG. 2, showing two tufts in an extended position and two tufts in a retracted position.

In a preferred embodiment as shown in FIGS. 1 to 3, for example, the cam shaft has a total of six lobes 45 thereon with the lobes identified as a, b, c, d, e, and f, respectively. When the cam shaft 42 is rotating, the lobes 45 may pass a given circumferential reference point in the order a, b, c, d, e, f. Alternatively, the lobes may pass a given circumferential reference point in any given order; one of which may be such as the order a, e, b, f, c, d. If the cam shaft were to have a total of four lobes, for example, the lobes 45 would be identified as a, b, c, and d and would pass a given circumferential reference point in the order a, b, c, d, or other order as chosen. If the cam shaft were to have a total of seven lobes, for example, the lobes 45 would be identified as a, b, c, d, e, f, and g and would pass a given circumferential reference point in the order a, b, c, d, e, f, g, or other order as chosen.

In general, all of the cam lobes that are spaced along a cam shaft are radially spaced around 360°. In general, that radial spacing of the cam lobes is even. Thus, where there are four lobes, one lobes would be found at each of 90°, 180°, 279°, and 0°/360°. Likewise, if there are six cam lobes, they would be spaced at 60°, 120°, 180° . . 0°/360°. As noted above, the lobes may pass a given circumferential reference point in any given order. When the lobes are evenly radially spaced, and particularly where the order of the rise and fall of the lobes is sequential along the cam shaft, there is a reduced vibration of the toothbrush head, and a reduced impact of the mass of the toothbrush head against the teeth and gums. Moreover, the power requirement for mechanical torque required to drive the cam shaft is reduced.

In an alternative embodiment, the cam shaft 42 is made from metal wire which is bent into its proper configuration. If the cam shaft is a bent metal wire, then the apertures 60 in the tuft blocks may be thinner. Otherwise, the camming action of the bent wire is much the same as a molded cam shaft.

The distal end 41 of the cam shaft 42 has a head portion 41a thereon that may fit into a co-operating snap connection 51 in the end wall 46 of the toothbrush head member 24.

Each of the tuft blocks 40 has a generally centrally located elongated aperture 60 therein that is adapted to receive the cam shaft therethrough. The aperture 60 is defined in part by a first cam receiving surface 61 and in part by a second cam receiving surface 62, which is opposed to the first cam receiving surface 61. The first and second cam receiving surfaces 61, 62 are separated by a distance generally equivalent to the distance "D", which is the diameter of the cam shaft 42 along the cam portion 43 thereof. The distance "D" between the first and second cam receiving surfaces is generally equivalent to the distance "D" that is the diameter of the lobes 45 so that the lobes 45 are retained within the aperture 60 without undue looseness. The cam shaft 42 interacts with the first cam receiving surface 61 of each of the tuft blocks 40 so as to drive the tuft blocks 40 from their retracted position to their extended position, and also with the second cam receiving surface 62 of each of the tuft blocks 40 so as to drive the tuft blocks 40 from their extended position to their retracted position. Any undue looseness between the lobes 45 and the first and second cam receiving surfaces 61, 62 would cause hammering of the first and second cam receiving surfaces by the lobes 45, which in turn would cause undue vibration and noise.

The apertures 60 are generally elongated in a direction that is transverse to both the central longitudinal axis 25 of the cam shaft 42 and the tuft axis 53 so as to accommodate laterally directed displacement of the lobes 45 of the cam shaft 42, and so as to preclude driving of the tuft blocks 40 in that same direction. Also, the single-axis reciprocating motion of the tuft blocks is assured.

The tuft blocks 40 are driven from their retracted positions to their extended positions by the rotation of the cam shaft 42 and the resulting interaction between the cam surfaces 44 of the lobes 45 and the first and second cam receiving surfaces 61, 62 of the tuft blocks 40. Preferably, the tuft blocks 40 move from their retracted position to their extended position a distance of between about 0.015 inches and 0.050 inches.

Figure 6:
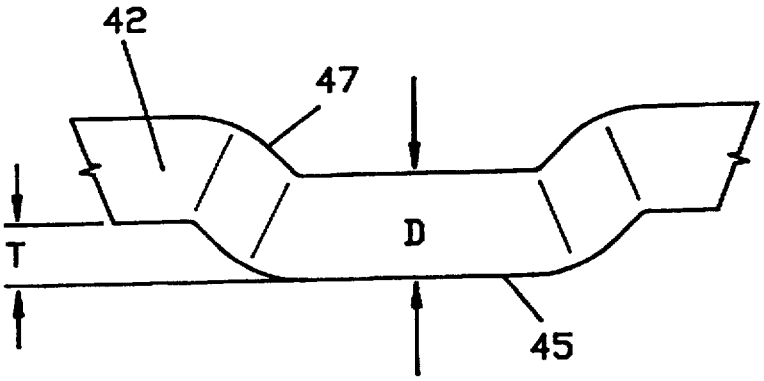
FIG. 6 is a partial view of the cam shaft found within the toothbrush head member.
Figure 7:
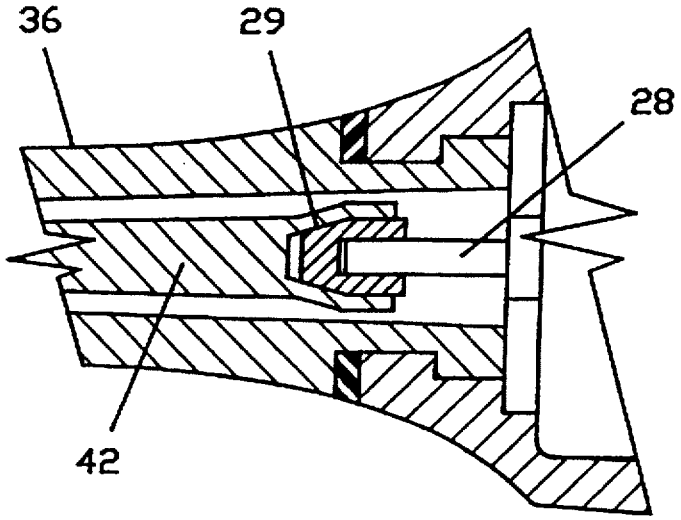
FIG. 7 is an enlarged partial view of the attachment means that is used to removably attach the toothbrush head member to the driving means.

It should be noted that the throw of the cam shaft 42, which is shown at "T" in FIG. 6, may be varied for different cam shafts, and therefore for different toothbrush head members 24, all of which may otherwise fit on the same housing member 22. The throw "T" may be short or long, or otherwise, to accommodate different users such as children or adults. Of course, the thickness, length, and stiffness of the bristles may also be varied, so that a wide variety of choices may be offered to prospective users both in respect of the bristle length, the bristle hardness, and the distance that the ends of the bristles move. Therefore, choices of a variety of toothbrush heads may be made available to various members of a family, for example, where a single driving unit or handle is used for all of the different toothbrush heads.

Covering the opening 35 in the head portion 38 of the toothbrush head member 24 is a flexible seal 70, which is attached in sealed relation to the toothbrush head member 24 and to the tuft blocks 40. The flexible seal 70 generally precludes foreign matter such as toothpaste, saliva, and so on, from entering the interior of the head portion 38 of the toothbrush head member 24 and ultimately reaching the tuft blocks 40 and cam shaft 42. The flexible seal 70 has a first lip portion 72 adapted for sealed engagement into an undercut 74 in the outer sides of the opposed side walls 44 of the head portion 38 of the toothbrush head member 24. The flexible seal 70 also has at least one second lip portion 76, each of which is in sealed engagement with a portion of each of the tuft blocks 40. In a preferred embodiment, the flexible seal 70 receives the tufts 52 through openings 78 at the bottom of depressions 77 that are formed therein. The openings 78 are created when the bristles 54 are inserted into the tuft blocks 40. Alternatively, each of the tuft blocks 40 may extend through a preformed opening in the flexible seal 70.

As can best be seen in FIG. 8, a portion of the flexible seal 70 enters the orifice 57 when the bristle tufts are inserted therein, as shown at 71. The pressure of the tufts 42 thereagainst helps create a snug seal between the flexible seal 70 and the tuft blocks 40. Essentially, a mechanical lock between the flexible seal 70 and each of the tuft blocks 40 is developed. Moreover, the flexible seal 70 can also act as a spring means to cause the tuft blocks 40 to return from their extended position to their retracted position.

Figure 11:
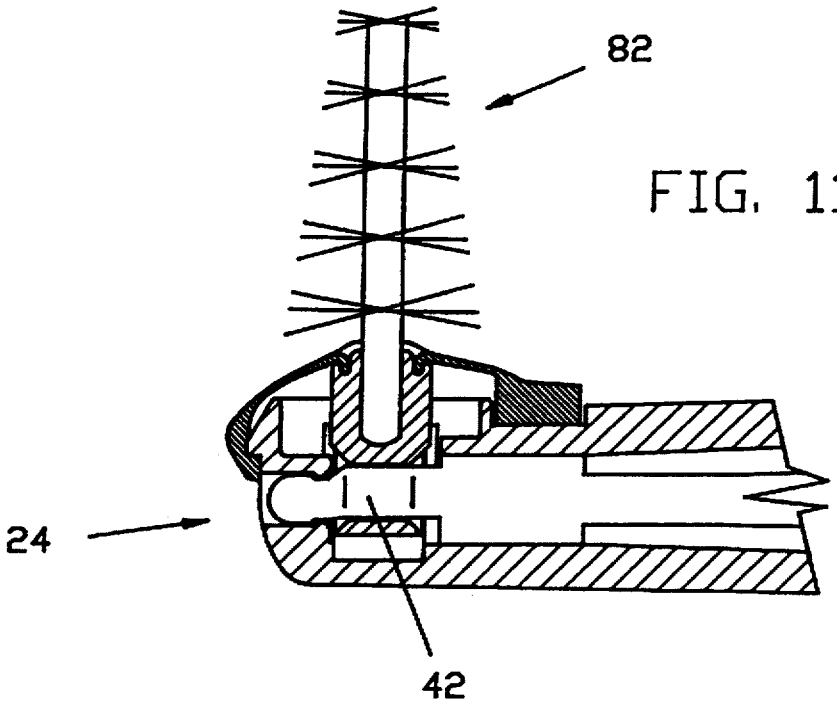
FIG. 11 is a side view of a proximal brush head, which is otherwise in keeping with the present invention.
Figure 12:
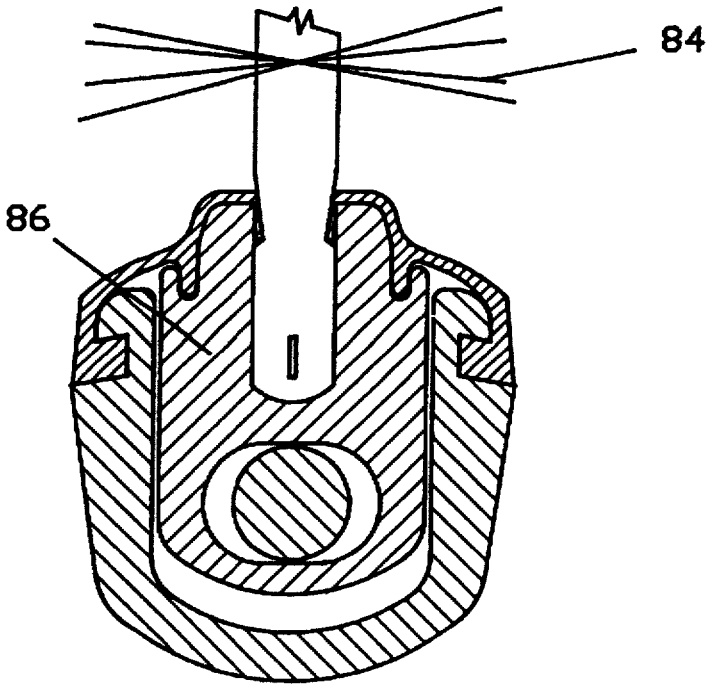
FIG. 12 is an enlarged cross-section of the proximal brush head of FIG. 11.

Reference is made now to FIGS. 11 and 12, which show a proximal brush which is otherwise in keeping with the present invention. Here, a single tufted proximal brush 82, having a plurality of tufts 84, is captured and held securely in a special tuft block 86 which is particularly designed for this purpose. The reciprocal action of the tuft block 86 comes as a consequence of it being driven by a single lobe cam shaft 42. The mounting and sealing arrangement for the proximal brush is otherwise as described above, and it serves the particular purposes intended for a proximal brush, especially in reaching the gingival and interproximal regions of the teeth and gums. The orientation of the proximal brush 82, perpendicular to the head portion 24, is particularly advantageous in reaching the rear molars of the user, when in use.

With reference now to FIG. 10, it is clear that the toothbrush of the present invention is brought into contact with the teeth 100 by the user in much the same way as an ordinary toothbrush is used. Thus, the bristles 54 are generally flexed at least to some extent even before any mechanical action of the toothbrush of the present invention occurs. For example, the amount of flex of the portion of a bristle tuft 59 may be quite significant, and is shown as the distance "F" by which the distal end 56 of the bristle group 59 has flexed from the axis of the tuft. After the toothbrush head is brought into position near the teeth in much the same manner as the user would use a manual toothbrush, and the toothbrush is powered so that the cam shaft is rotating as discussed above, the tuft blocks 40 will travel from their retracted position to their extended position in the manner discussed above. Because the tuft blocks 40 are driven from their retracted position to their extended position by the cam shaft 42, which is a positive mechanical driving means, the bristles 54 will continue to be forced against the teeth 100 and will flex even more. This will, in turn, cause the distal ends 56 of the bristles 54 to move laterally along the surface of the teeth 100, where the lateral motion of the distal ends 56 of the bristles is relative to the longitudinal axes 53 of the bristles 54. As noted above, the lateral motion of the distal end 56 of the bristles 54 will essentially chisel unwanted substances, plaque, and so on away from the surface of the teeth, and thereafter they are removed away from the teeth. Because there is a positive mechanical linkage between the cam shaft 42 and the bristles 54, there is thereby ensured the lateral motion of the distal ends 56 of the bristles, thereby assuring the continuous cleaning action of the bristles against the teeth. Moreover, as the tuft blocks move towards their retracted position, there will be a sweeping or scrubbing action of at least the ends of the bristles against the teeth, to assist in the removal of foreign matter that has otherwise been dislodged from the surfaces of the teeth. The oscillating or back-and-forth motion of the distal ends 56 of the bristles is such as that which is indicated by the doubled-headed arrow 61 in FIG. 10.

The frequency of strokes of the tuft blocks is preferably greater than 2000 times per minute, with a preferred range between about 5000 times per minute and 10,000 times per minute, with an ideal frequency being about 6000 times per minute. It should be noted that, even at a stroke frequency of about 6000 times per minute, or more, there is no undue or undesirable vibration which may cause discomfort to the insides of the cheeks and lips of the user. This frequency coupled with the short stroke of the bristles, precludes any undue abrasion to the gums or gingival regions, which might cause discomfort or bleeding.

For example, in the case where there may be four tuft blocks, each having four tufts, where each tuft has 64 bristles, there are therefore 1024 bristles present for a cleaning or cleansing action against the teeth. If the stroke frequency of the tuft blocks is 6000 times per minute, then there will be 102,400 individual bristle strokes with the concomitant chiseling action of the bristles, per second. In a toothbrush of the present-invention having six tuft blocks, each with 4 tufts of 64 bristles, there would be 153,600 individual bristle strokes, each with the concomitant chiseling action, per second.

In an alternative embodiment, it is contemplated that spring means—or even the reaction of the bristles being pressed against the teeth and gums—could be used to help return the tuft blocks from their extended position to their retracted position. In this alternative embodiment, it is not necessary that the apertures 60 in the tuft blocks 40 would have a second receiving surface 62. The spring means or reactive pressure from the teeth and gums could, themselves, be used to force the tuft blocks to return to their retracted position, without being driven to the retracted position such as by the lobes of the cam shaft driving against the second receiving surfaces 62 of the tuft blocks. In any event, an assured and positive driving motion of the tuft blocks away from their extended position towards their retracted position is assured.

It is, of course, possible that oscillating cams may be used rather than continuously rotating cam shafts, to lift the tuft blocks at least towards their extended position, with such as the spring means or reactive pressure from the teeth and gums being utilized to drive the tuft blocks towards their retracted position. In general, the cam shaft may be oscillated, in these circumstances, through an oscillation arc of between 90° and 180° so as to impart vertical motion to the tuft block.

It is noted that other driving means may be provided for rotating the cam shaft. For example, a water-pressure turbine could be used, where the toothbrush can be driven from a turbine that is powered by the water pressure of the running water being used as the teeth are being cleaned. An air-driven turbine could also be used.

Other modifications and alterations may be used in the design and manufacture of the mechanical toothbrush of the present invention without departing from the spirit and scope of the accompanying claims.

What is claimed is:

1. A power driven mechanical toothbrush, comprising:

a cam shaft adapted to be rotatably driven, and having a central longitudinal axis;

a driving means adapted to rotatably drive said cam shaft;

a toothbrush head member having a centrally disposed longitudinal head axis, a bottom wall, an end wall, a pair of opposed side walls, and guide means mounted within said toothbrush head member;

a main housing adapted to retain said driving means therein, and to retain said cam shaft in operative relation with said driving means, and having said toothbrush head member mounted thereon;

at least one tuft block retained generally within said toothbrush head member and mounted in driving relationship with said cam shaft and extending laterally outwardly from said central longitudinal axis, wherein said at least one tuft block has at least one tuft of bristles secured within said tuft block and extending upwardly therefrom, said bristles having a distal end at a distance from said tuft block, said bristles in said at least one tuft being generally parallel to one another, said at least one tuft having a longitudinal tuft axis located generally along the centre thereof;

wherein said toothbrush head member is adapted to receive and retain said at least one tuft block in sliding relation therein such that said at least one tuft block slides linearly in a direction parallel to said longitudinal tuft axis as guided by said guide means within said head member, between a retracted position and an extended position;

wherein said at least one tuft block is driven from said retracted position to said extended position by the rotation of said cam shaft and the resulting interaction between said cam shaft and said at least one tuft block; and wherein, in use, said bristles are brought into contact with the teeth by a user, before the respective said at least one tuft block reaches said extended position so as to thereby flex said bristles and cause a lateral motion of the distal end thereof along the surface of the teeth, and so as to thereby to remove unwanted substances from the teeth.

2. The toothbrush of claim 1, wherein said at least one tuft block has a plurality of tufts, each tuft having its own longitudinal axis, with each of said longitudinal tuft axes being substantially parallel one to another.

3. The toothbrush of claim 2, wherein said head member is elongated, and wherein there is a plurality of tuft blocks disposed along said longitudinal axis of said toothbrush head member, with said longitudinal tuft axes being substantially perpendicular to said longitudinal head axis of said elongated head member and with each of said longitudinal tuft axes being substantially parallel one to another; and wherein there is a respective cam lobe disposed along said cam shaft for each said tuft block.

4. The toothbrush of claim 3, wherein said plurality of tuft blocks is substantially juxtaposed one to another.

5. The toothbrush of claim 4, wherein said guide means comprises pairs of opposed guide rails extending inwardly from said opposed side walls.

6. The toothbrush of claim 5, wherein each of said tuft blocks has an aperture therein adapted to receive said cam shaft therethrough, said aperture being defined in part by a first cam receiving surface, wherein said cam shaft interacts with said first cam receiving surface of each of said tuft blocks so as to drive said tuft blocks from said retracted position to said extended position.

7. The toothbrush of claim 6, wherein said aperture in each of said tuft blocks is elongated in a direction that is transverse to both of said central longitudinal axis of said cam shaft and to the direction of said tuft axes.

8. The toothbrush of claim 7, wherein said cam shaft has a plurality of lobes that are substantially circular in cross-section and have a diameter "D", and wherein said lobes are connected by connecting portions having a maximum thickness "D".

9. The toothbrush of claim 8, wherein said plurality of lobes are radially spaced from a central axis of said cam shaft so that each of said lobes will drive its respective tuft block to a predetermined extent away from said central axis of said cam shaft; and wherein said predetermined extent is selectable from one cam shaft of said toothbrush head member to another cam shaft of another toothbrush head member, so as to thereby permit differing cleaning actions for various respective ones of said toothbrush head member.

10. The toothbrush of claim 8, wherein said connecting portions are ramped so as to facilitate positioning of said cam shaft into the respective aperture in each of said tuft blocks.

11. The toothbrush of claim 10, wherein said cam shaft is made from a metal wire.

12. The toothbrush of claim 8, wherein each of said apertures is further defined by a second cam receiving surface, which is opposed to said first cam receiving surface, wherein said first and second cam receiving surfaces are separated by a distance generally equivalent to the distance "D".

13. The toothbrush of claim 7, wherein said cam shaft is oscillated through an oscillation arc of from 90° to 180°, so as to impart vertical motion to said tuft block.

14. The toothbrush of claim 4, wherein each tuft block has four tufts of bristles which include two inner tufts and two outer tufts, with one inner tuft and one outer tuft disposed at each side of said longitudinal head axis.

15. The toothbrush of claim 3, wherein there are more than three and fewer than nine juxtaposed tuft blocks.

16. The toothbrush of claim 3, wherein there are six juxtaposed tuft blocks.

17. The toothbrush of claim 16, wherein said cam shaft has a total of six lobes identified as a, b, c, d, e, and f, respectively, and wherein when said cam shaft is rotating, the lobes pass a given circumferential reference point in the order a, e, b, f, c, d.

18. The toothbrush of claim 3, wherein each of said respective cam lobes disposed along said cam shaft is radially spaced through a total cam lobe radial spacing of 360°.

19. The toothbrush of claim 18, wherein said cam lobes are evenly radially spaced.

20. The toothbrush of claim 1, wherein said at least one tuft block moves from said retracted position to said extended position a distance of between 0.015 inches and 0.050 inches.

21. The toothbrush of claim 1, wherein there is only a single tuft block, having one proximal brush attached thereto.

22. The toothbrush of claim 1, further comprising a flexible seal attached in sealed relation to said toothbrush head member and to said at least one tuft block, and wherein said flexible seal receives said at least one tuft block through a respective opening therein, said flexible seal being thereby adapted to preclude foreign matter from entering the interior of said toothbrush head member.

23. The toothbrush of claim 22, wherein said flexible seal is mechanically attached to said toothbrush head member, and is further mechanically attached to said at least one tuft block, so as to be in sealed engagement with said toothbrush head member and said at least one tuft block.

24. The toothbrush of claim 22, wherein said flexible seal acts as a spring means.

25. The toothbrush of claim 1, further comprising a flexible seal attached in sealed relation to said toothbrush head member and to said at least one tuft block, and wherein said flexible seal receives said tufts through respective openings therein for each of said tufts, said flexible seal being thereby adapted to preclude foreign matter from entering the interior of said toothbrush head member.

26. The toothbrush of claim 25, further comprising a flexible seal attached in sealed relation to said toothbrush head member and to said at least one tuft block, and wherein said flexible seal receives said tufts through respective openings therein for each of said tufts, said flexible seal being thereby adapted to preclude foreign matter from entering the interior of said toothbrush head member.

27. The toothbrush of claim 26, wherein said flexible seal has a first lip portion adapted for sealed engagement into an undercut in the outer sides of said opposed walls of said toothbrush head member, and a second lip portion for said at least one tuft block, with said second lip portion being in sealed engagement with a portion of said at least one tuft block.

28. The toothbrush of claim 25, wherein at least a portion of said flexible seal contacts at least a portion of the respective opening for each of said tufts, so as to thereby create a snug seal between said flexible seal, each of said tufts, and said at least one tuft block.

29. The toothbrush of claim 25, wherein said flexible seal acts as a spring means, whereby said at least one tuft block is biased towards said retracted position.

30. The toothbrush of claim 1, wherein said cam shaft is locked into assembled position by way of a snap connection into said end wall of said toothbrush head member.

31. The toothbrush of claim 1, wherein the frequency of stroke of said at least one tuft block is greater than 2000 times per minute.

32. The toothbrush of claim 1, wherein the frequency of stroke of said at least one tuft block is between about 2000 and 10,000 times per minute.

33. The toothbrush of claim 32, wherein the frequency of stroke of said at least one tuft block is about 6000 times per minute.

34. The toothbrush of claim 33, wherein said bristles extend outwardly from said at least one tuft block a distance of about ⅜ inches.

35. The toothbrush of claim 33, wherein said bristles have a diameter of 0.005 to 0.008 inches.

36. The toothbrush of claim 1, wherein said driving means is an electrically powered motor.

37. The toothbrush of claim 1, further comprising at least one spring member, whereby said at least one tuft block is biased towards said retracted position.

*38. The toothbrush of claim 1, wherein the toothbrush head member is detachably mounted on the main housing.*

*39. A toothbrush head member, comprising:*

*a housing, including a centrally disposed longitudinal head axis, a bottom wall, an end wall, a pair of opposed side walls, and guide means mounted within said toothbrush head member;*

*a cam shaft retained in said housing, said cam shaft having a central longitudinal axis and being adapted to be rotatably driven by a power unit;*

*at least one tuft block retained generally in said housing wherein said at least one tuft block having at least one tuft of bristles secured within said tuft block and extending upwardly therefrom, said at least one tuft having a longitudinal tuft axis located generally along the centre thereof;*

*wherein said housing is adapted to receive and retain said at least one tuft block in sliding relation therein such that said at least one tuft block slides linearly in a direction parallel to sad longitudinal tuft axis as guided by said guide means within said head member, between a retracted position and an extended position; and*

*wherein said at least one tuft block is driven from said retracted position to said extended position by the rotation of said cam shaft and the resulting interaction between said cam shaft and said at least one tuft block.*

*40. The toothbrush head member of claim 39, wherein at least one tuft block is mounted in driving relationship with the cam shaft and extends laterally outwardly from the central longitudinal axis.*

*41. The toothbrush head member of claim 40, wherein said at least one tuft block has a plurality of tufts, each tuft having its own longitudinal axis, with each of said longitudinal tuft axes being substantially parallel one to another.*

*42. The toothbrush head member of claim 41, wherein said at least one tuft block moves from said retracted position to said extended position a distance of between 0.015 inches and 0.050 inches.*

*43. The toothbrush head member of claim 41, wherein there is only a single tuft block, having one proximal brush attached thereto.*

*44. The toothbrush head member of claim 41, further comprising a flexible seal in sealed relation to said toothbrush head member and to said at least one tuft block, and wherein said flexible seal receives said at least one tuft block through a respective opening therein, said flexible seal being thereby adapted to preclude foreign matter from entering the interior of said toothbrush head member.*

*45. The toothbrush head member of claim 44, wherein said flexible seal is mechanically attached to said toothbrush head member, and is further mechanically attached to said at least one tuft block, so as to be in sealed engagement with said toothbrush head member and said at least one tuft block.*

*46. The toothbrush head member of claim 45, wherein said flexible seal acts as a spring means.*

*47. The toothbrush head member of claim 41, further comprising a flexible seal attached in sealed relation to said toothbrush head member and to said at least one tuft block, and wherein said flexible seal receives said tufts through respective openings therein for each of said tufts, said flexible seal being thereby adapted to preclude foreign matter from entering the interior of said toothbrush head member.*

*48. The toothbrush head member of claim 47, further comprising a flexible seal attached in sealed relation to said toothbrush head member and to said at least one tuft block, and wherein said flexible seal receives said tufts through respective openings therein for each of said tufts, said flexible seal being thereby adapted to preclude foreign matter from entering the interior of said toothbrush head member.*

*49. The toothbrush head member of claim 48, wherein said flexible seal has a first lip portion adapted for sealed engagement into an undercut in the outer sides of said opposed walls of said toothbrush head member, and a second lip portion for said at least one tuft block, with said second lip portion being in sealed engagement with a portion of said at least one tuft block.*

*50. The toothbrush head member of claim 48, wherein said flexible seal acts as a spring means, whereby said at least one tuft block is biased towards said retracted position.*

*51. The toothbrush head member of claim 47, wherein at least a portion of said flexible seal contacts at least a portion of the respective opening for each of said tufts, so as to thereby create a snug seal between said flexible seal, each of said tufts, and said at least one tuft block.*

*52. The toothbrush head member of claim 41, wherein said cam shaft is locked into assembled position by way of a snap connection into said end wall of said toothbrush head member.*

*53. The toothbrush head member of claim 41, wherein the frequency of stroke of said at least one tuft block is greater than 2000 times per minute.*

*54. The toothbrush head member of claim 41, wherein the frequency of stroke of said at least one tuft block is between about 2000 and 10,000 times per minute.*

*55. The toothbrush head member of claim 54, wherein the frequency of stroke of said at least one tuft block is about 6000 times per minute.*

*56. The toothbrush head member of claim 55, wherein said bristles extend outwardly from said at least one tuft block a distance of about ⅜ inches.*

*57. The toothbrush head member of claim 55, wherein said bristles have a diameter of 0.005 to 0.008 inches.*

*58. The toothbrush head member of claim 41, wherein said power unit is an electrically powered motor.*

*59. The toothbrush head member of claim 41, further comprising at least one spring member, whereby said at least one tuft block is biased towards said retracted position.*

*60. The toothbrush head member of claim 41, wherein said housing includes an elongated portion, and wherein there is a plurality of tuft blocks disposed along said longitudinal axis of said housing, with said longitudinal tuft axes being substantially perpendicular to said longitudinal head axis; and wherein there is a cam lobe disposed along said cam shaft for each said tuft block.*

*61. The toothbrush head member of claim 60, wherein said plurality of tuft blocks is substantially juxtaposed one to another.*

*62. The toothbrush head member of claim 61, wherein said guide means comprises pairs of opposed guide rails extending inwardly from said opposed side walls.*

*63. The toothbrush head member of claim 62, wherein each of said tuft blocks has an aperture therein adapted to receive said cam shaft therethrough, said aperture being defined in part by a first cam receiving surface, wherein said cam shaft interacts with said first cam receiving surface of each of said tuft blocks so as to drive said tuft blocks from said retracted position to said extended position.*

*64. The toothbrush head member of claim 63, wherein said aperture in each of said tuft blocks is elongated in a direction that is transverse to said central longitudinal axis of said cam shaft and to the direction of said tuft axes.*

*65. The toothbrush head member of claim 64, wherein said cam lobes are substantially circular in cross-section and are connected by connecting portions having no greater diameter than the diameter of the circular cross-section.*

*66. The toothbrush head member of claim 65, wherein said lobes are radially spaced from a central axis of said cam shaft so that each of said lobes will drive its respective tuft block to a predetermined extent away from said central axis of said cam shaft.*

*67. The toothbrush head member of claim 65, wherein said connecting portions are ramped so as to facilitate positioning of said cam shaft into the respective aperture in each of said tuft blocks.*

*68. The toothbrush head member of claim 67, wherein said cam shaft is a metal wire.*

*69. The toothbrush head member of claim 65, wherein each of said apertures is further defined by a second cam receiving surface, which is opposed to said first cam receiving surface, wherein said first and second cam receiving surfaces are separated by a distance generally equivalent to the diameter of the circular cross-section of the cam lobes.*

*70. The toothbrush head member of claim 64, wherein said cam shaft can be oscillated through an oscillation arc of from 90° to 180° so as to impart vertical motion to each of said tuft blocks.*

*71. The toothbrush head member of claim 60, wherein each of said tuft blocks has two inner tufts and two outer tufts, one inner tuft and one outer tuft disposed at each side of said longitudinal head axis.*

*72. The toothbrush head member of claim 60, wherein there are more than three and fewer than nine juxtaposed tuft blocks.*

*73. The toothbrush head member of claim 60, wherein there are six juxtaposed tuft blocks.*

*74. The toothbrush head member of claim 73, wherein said cam shaft has a total of six lobes identified as a, b, c, d, e, and f, respectively, and wherein when said cam shaft is rotating, the lobes pass a given circumferential reference point in the order a, e, b, f, c, d.*

*75. The toothbrush head member of claim 60, wherein each of said cam lobes disposed along said cam shaft is radially spaced through a total cam lobe radial spacing of 360°.*

*76. The toothbrush head member of claim 75, wherein said cam lobes are evenly radially spaced.*

*77. A toothbrush comprising:*

*an elongated hollow shaft having a head portion at one axial end thereof and a bore;*

*a cam shaft co-axially disposed for rotation in the bore of the hollow shaft, one axial end of the cam shaft being adapted for driving connection with a power unit and the other axial end of the cam shaft defining a plurality of adjacent cam surfaces each cam surface being disposed to define a path of rotation that is separate from an axially adjacent cam surface; and*

*a plurality of tuft blocks disposed in the head portion of the hollow shaft for independent reciprocal movement on parallel axes perpendicular to the cam shaft axis, each tuft block carrying at least one tuft of bristles extending along the axis of reciprocation and each tuft block being engaged by a respective one of the cam surfaces to generate the reciprocal movement in response to the rotation of the cam shaft.*

*78. The toothbrush of claim 77, further comprising a power unit which includes a housing, a motor, including a rotatable drive shaft disposed for selective engagement by the one axial end of the cam shaft, and electric circuitry for selectively connecting the motor to a power source, wherein said hollow shaft is detachably mounted onto the housing.*

*79. The toothbrush of claim 77 comprising four tuft blocks.*

*80. The toothbrush of claim 77 comprising six tuft blocks.*

*81. The toothbrush of claim 77, wherein the cam surfaces are substantially equidistantly radially spaced about the cam shaft.*

*82. The toothbrush of claim 77, wherein each tuft block comprises an aperture therein for receiving said cam shaft therethrough, said aperture being elongated in a direction transverse to both the axis of reciprocation and to the cam shaft axis.*

* * * * *